United States Patent
Wu et al.

(10) Patent No.: US 9,084,958 B2
(45) Date of Patent: Jul. 21, 2015

(54) COLLECTING DEVICE FOR GASES AND AEROSOL, METHODS OF MAKING, AND METHODS OF USE

(75) Inventors: Chang-Yu Wu, Gainesville, FL (US); Yu-Mei Hsu, Hukou Township, Hsin-Chu County (TW); Alex Theodore, Plantation, FL (US); Lin Shou, Gainesville, FL (US); Danielle Lyon Hall, Sarasota, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 13/876,305

(22) PCT Filed: Oct. 17, 2011

(86) PCT No.: PCT/US2011/056535
§ 371 (c)(1),
(2), (4) Date: Mar. 27, 2013

(87) PCT Pub. No.: WO2012/054382
PCT Pub. Date: Apr. 26, 2012

(65) Prior Publication Data
US 2013/0192463 A1    Aug. 1, 2013

Related U.S. Application Data

(60) Provisional application No. 61/393,978, filed on Oct. 18, 2010.

(51) Int. Cl.
| | | |
|---|---|---|
| B01D 50/00 | (2006.01) | |
| B01D 53/04 | (2006.01) | |
| G01N 1/22 | (2006.01) | |
| B01D 46/00 | (2006.01) | |

(52) U.S. Cl.
CPC ........ B01D 53/0407 (2013.01); B01D 46/0036 (2013.01); G01N 1/2205 (2013.01); G01N 1/2208 (2013.01)

(58) Field of Classification Search
CPC ........... B01D 53/0407; B01D 46/0036; B01D 1/2208; B01D 1/2205
USPC ........... 55/320, 485–486, 522, 528, 462, 465; 95/285–287, 232–240; 73/863.12, 73/863.23; 96/154
See application file for complete search history.

(56) References Cited

U.S. PATENT DOCUMENTS

| | | |
|---|---|---|
| 4,455,881 A | 6/1984 | Clark et al. |
| 4,473,296 A | 9/1984 | Shofner et al. |
| 4,926,679 A | 5/1990 | Dewhurst |
| 4,941,899 A | 7/1990 | Liu |
| 5,302,191 A | 4/1994 | Koutrakis et al. |
| 5,437,198 A | 8/1995 | John |
| 5,498,271 A | 3/1996 | Marple et al. |
| 5,551,311 A | 9/1996 | Ogden et al. |
| 5,596,405 A | 1/1997 | Seltzer et al. |
| 5,646,357 A | 7/1997 | Ogden et al. |
| 5,783,756 A | 7/1998 | Xiong et al. |
| 5,870,190 A | 2/1999 | Unger |
| 6,321,608 B1 | 11/2001 | Wagner et al. |
| 6,431,014 B1 | 8/2002 | Liu et al. |
| 6,506,345 B1 | 1/2003 | Lee et al. |
| 6,584,865 B1 | 7/2003 | Doherty et al. |
| 6,786,105 B1 | 9/2004 | Sioutas |
| 6,890,372 B2 | 5/2005 | Dasgupta et al. |
| 7,029,921 B2 | 4/2006 | Lee et al. |
| 7,100,423 B2 | 9/2006 | Trenholm |
| 7,155,988 B2 | 1/2007 | Cole et al. |
| 7,458,284 B2 | 12/2008 | Shih et al. |
| 7,513,940 B2 | 4/2009 | Milcham et al. |
| 7,537,629 B2 | 5/2009 | Shih et al. |
| 7,572,419 B2 | 8/2009 | Cooper et al. |
| 7,578,973 B2 | 8/2009 | Call et al. |
| 7,621,171 B2 | 11/2009 | O'Brien |
| 7,700,045 B2 | 4/2010 | Skarping et al. |
| 2005/0000363 A1* | 1/2005 | Minemura et al. ............... 96/154 |
| 2005/0279181 A1 | 12/2005 | Trakumas et al. |
| 2006/0172428 A1 | 8/2006 | McDermott et al. |
| 2008/0134894 A1 | 6/2008 | Tsai et al. |

FOREIGN PATENT DOCUMENTS

EP        1750113 A1    2/2007

OTHER PUBLICATIONS

Dennis R. Fritz; A Fabric Denuder for Sampling Semi-Volatile Species; J. Air & Waste Manage. Assoc., 2000, 50, pp. 981-992.
Fritz, et al.; A Passive Flux Denuder for Evaluating Emissions of Ammonia at a Dairy Farm; J. Air & Waste Manage. Assoc., Aug. 2003, 53(8); 937-45.
Mikuska, et al.; Artifact Free Denuder Method for Sampling of Carbonaceous Aerosols; EGS—AGU—EUG—Joint Assembly, Abstracts from the Meeting held in Nice, France, Apr. 6-11, 2003, abstract # 5873.
Ruiz, et al.; A Counter-Current Parallel-Plate Membrane Denuder for the Non-Specific Removal of Trace Gases; Environ Sci Technol. Aug. 15, 2006; 40(16): 5058-63.
Xiao-Ying, et al.; Particulate Nitrate Measurement Using Nylon Filters; Journal of the Air & Waste Management Associate, Aug. 2005.
Chuen-Jinn, et al.; Simultaneous Sampling of Gas- and Aerosol-Phase TDI with a Triple Filter System; Journal of the Air & Waste Management Associate, Oct. 2003.
The International Search Report and Written Opinion dated May 15, 2012.
Koutrakis, et al., "Determination of Aerosol Strong Acidity Losses Due to Interactions of Collected Particles: Results from Laboratory and Field Studies,"Atmospheric Environment, 1992, vol. 26A, No. 6, pp. 987-995.

* cited by examiner

Primary Examiner — Dung H Bui
(74) Attorney, Agent, or Firm — Thomas Horstemeyer, LLP

(57) ABSTRACT

Embodiments of the present disclosure provide for collection devices, methods of making collection devices, methods of collecting gases and aerosol particles, and the like.

13 Claims, 14 Drawing Sheets

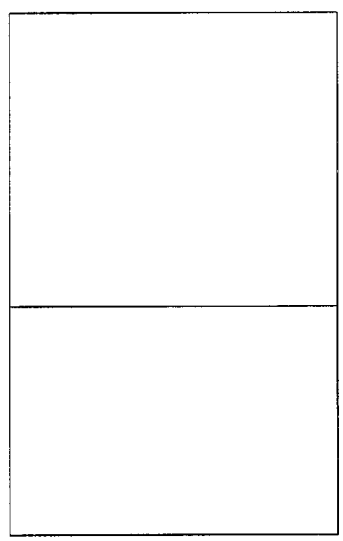 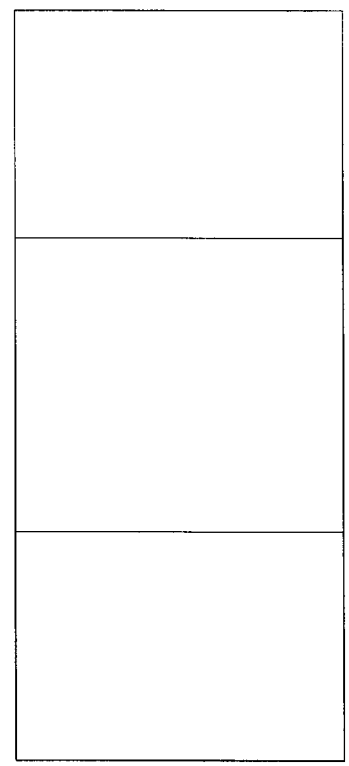
FIG. 1.1    FIG. 1.2

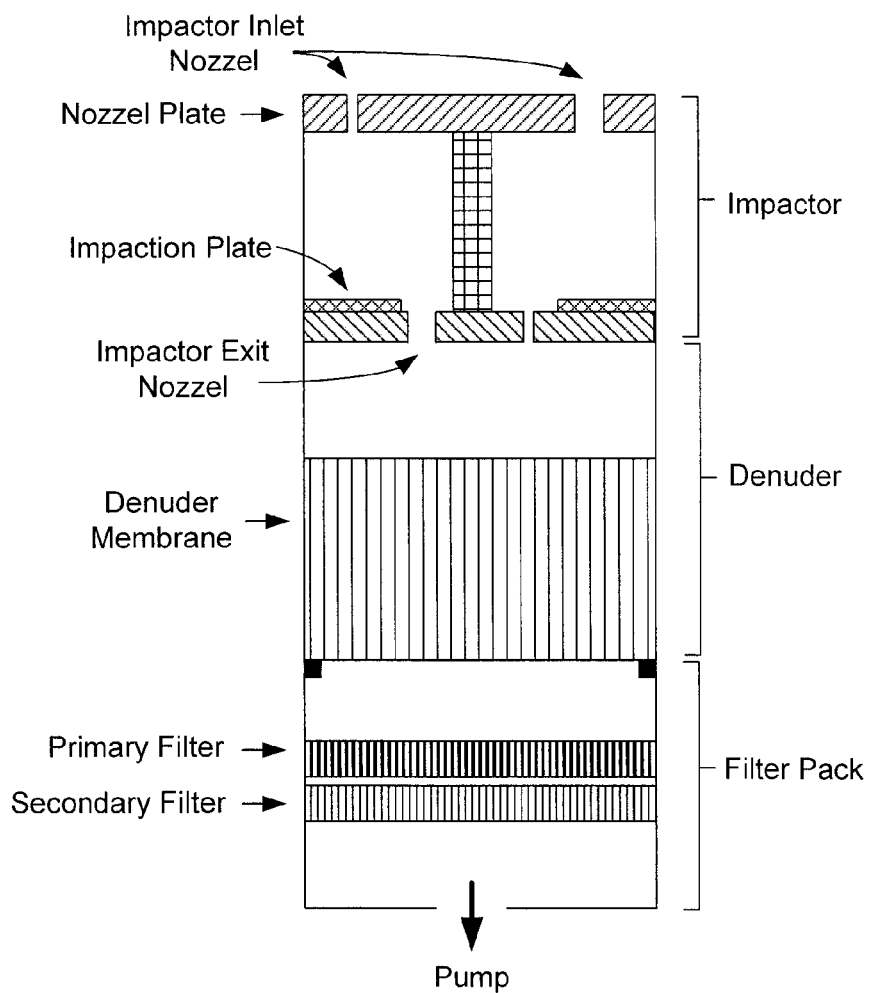
FIG. 1.3

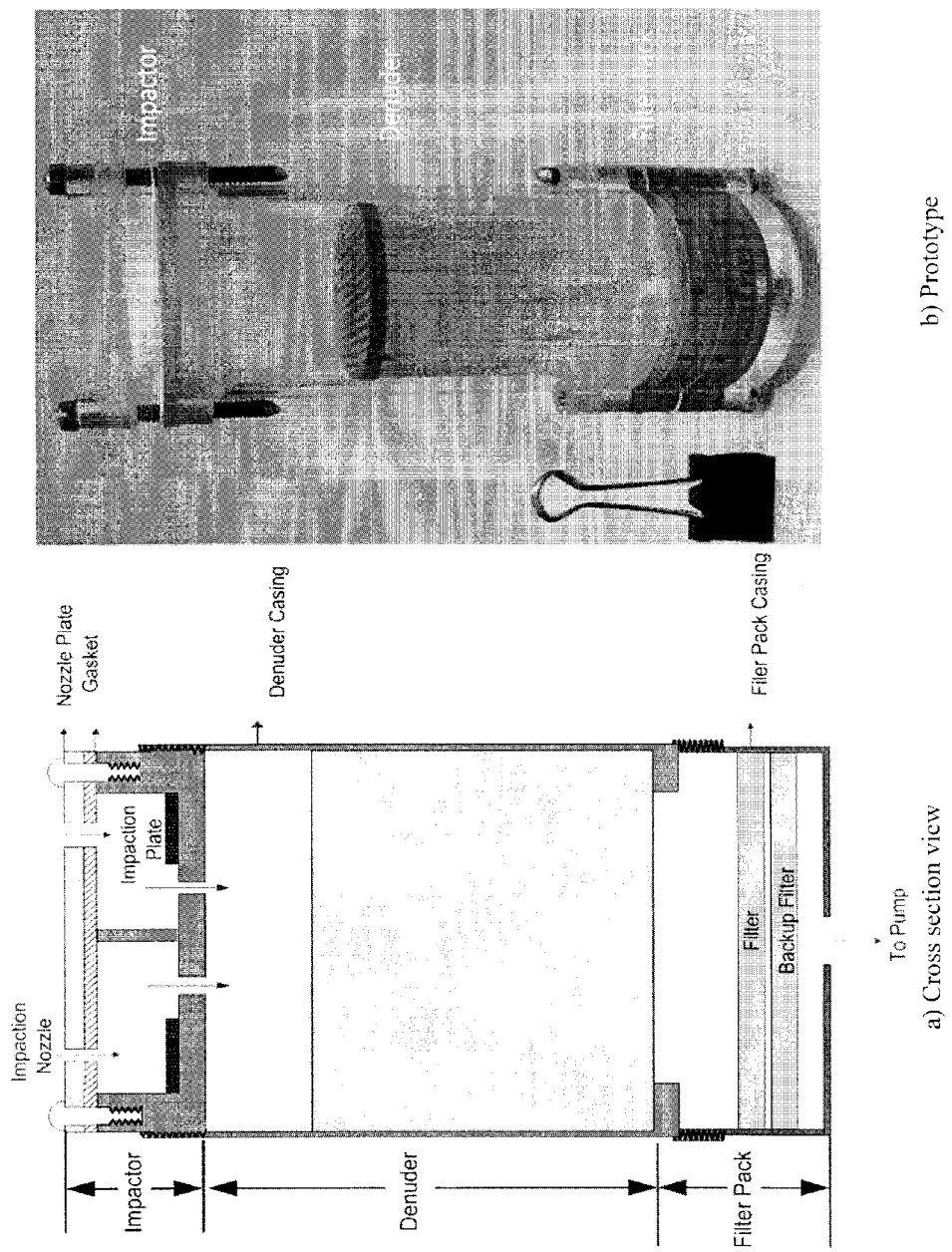
FIG. 2.1

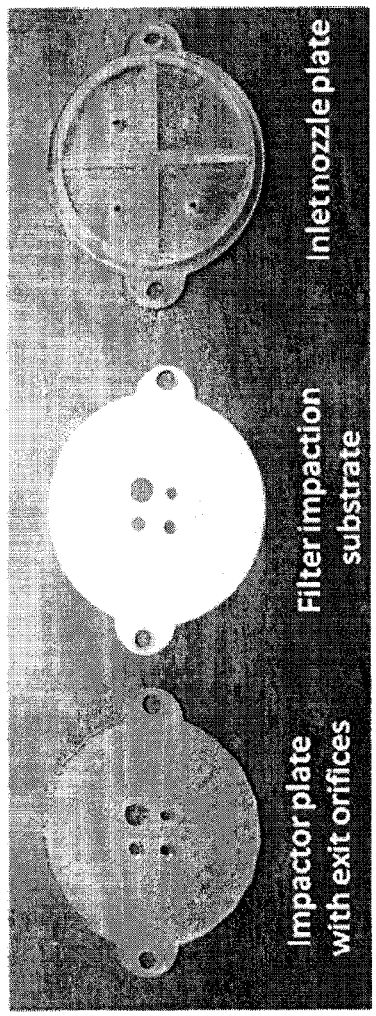
FIG. 2.2
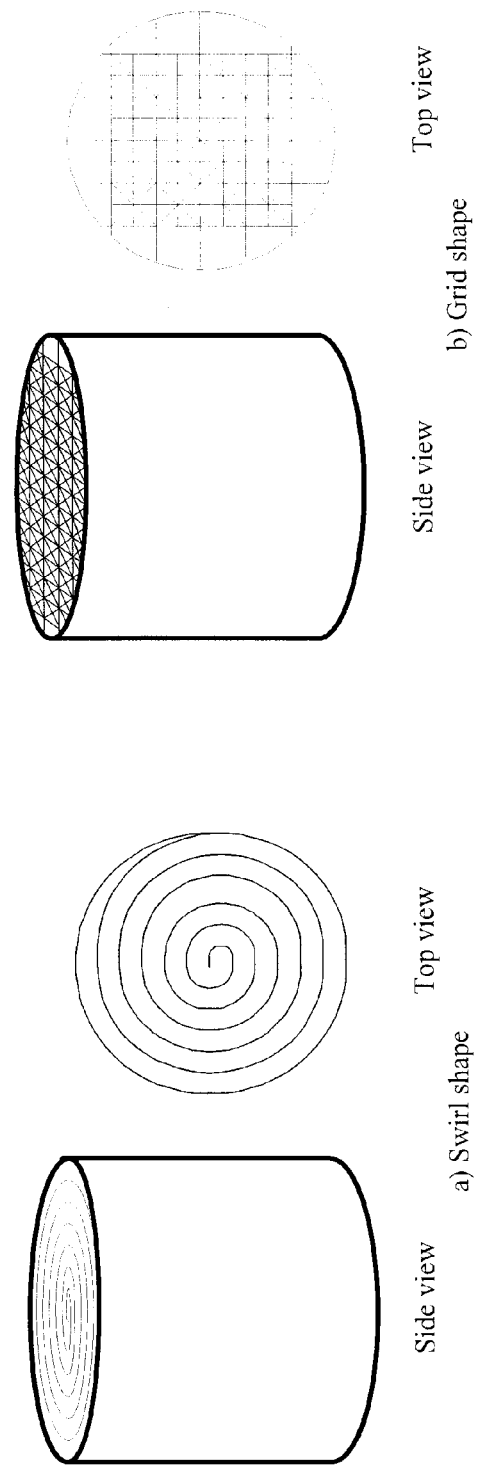
FIG. 2.3

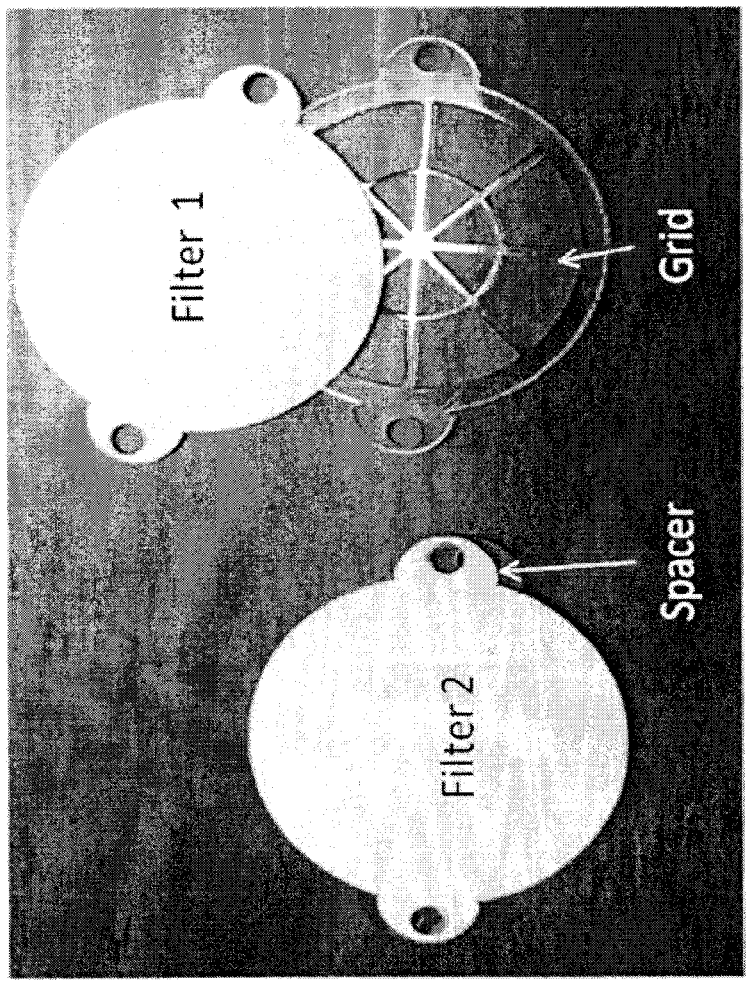
FIG. 2.5
Structure of the filter pack
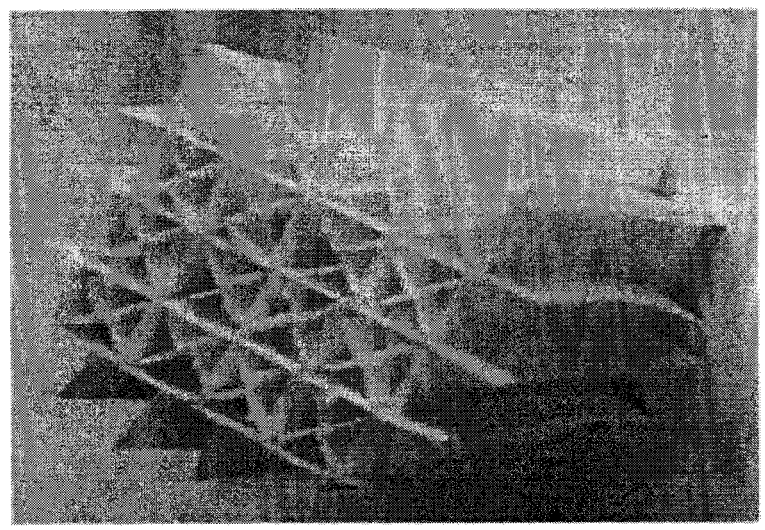
FIG. 2.4
Structure of the denuder

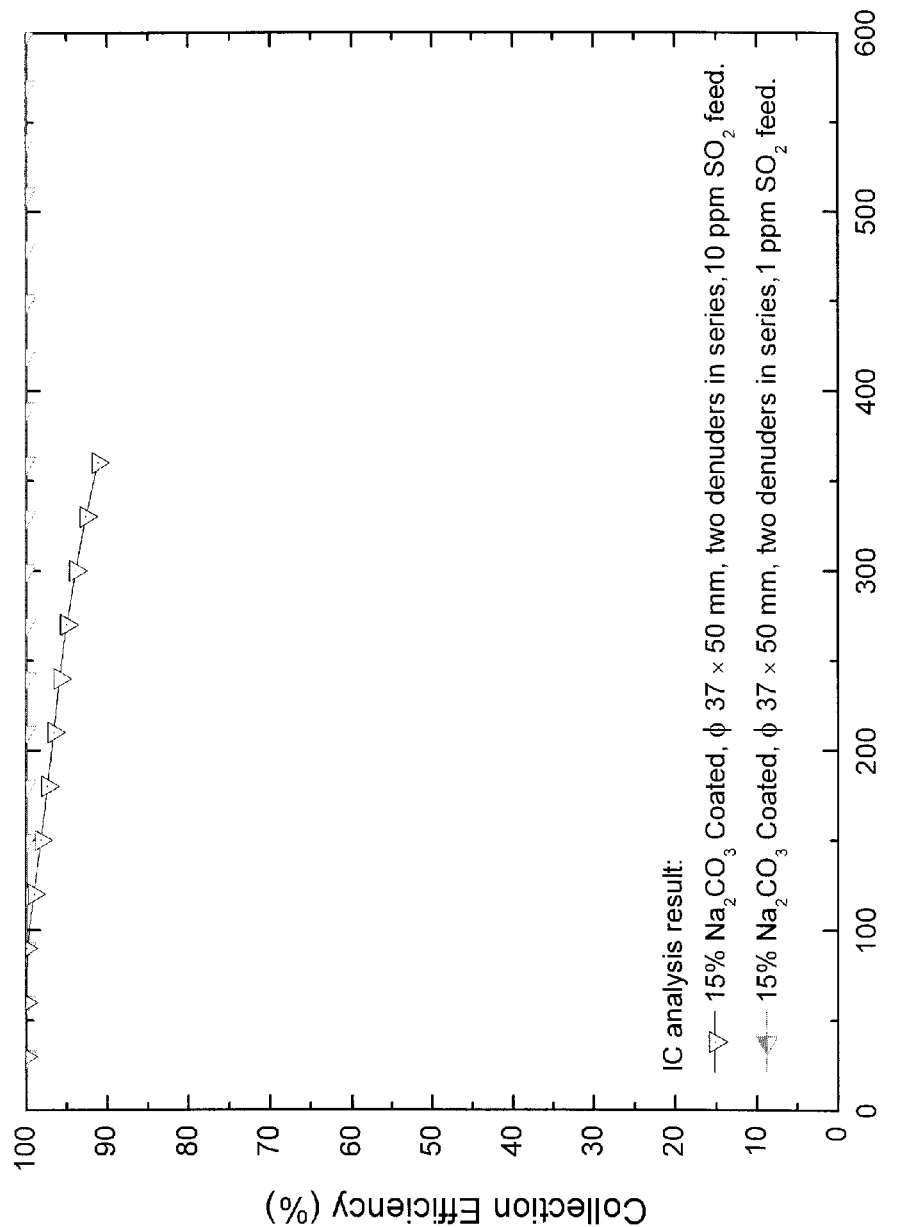
FIG. 2.6

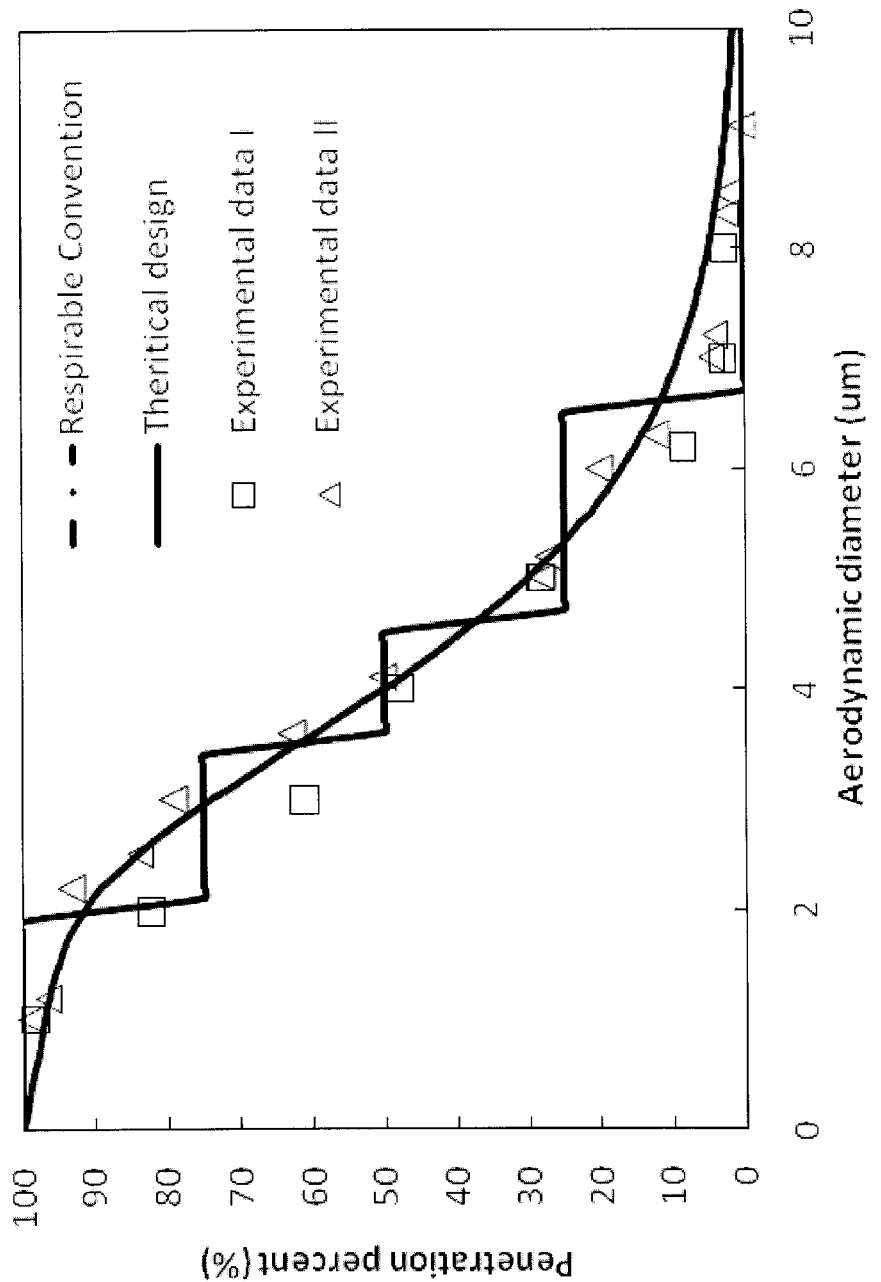
FIG. 2.7

FIG. 2.8

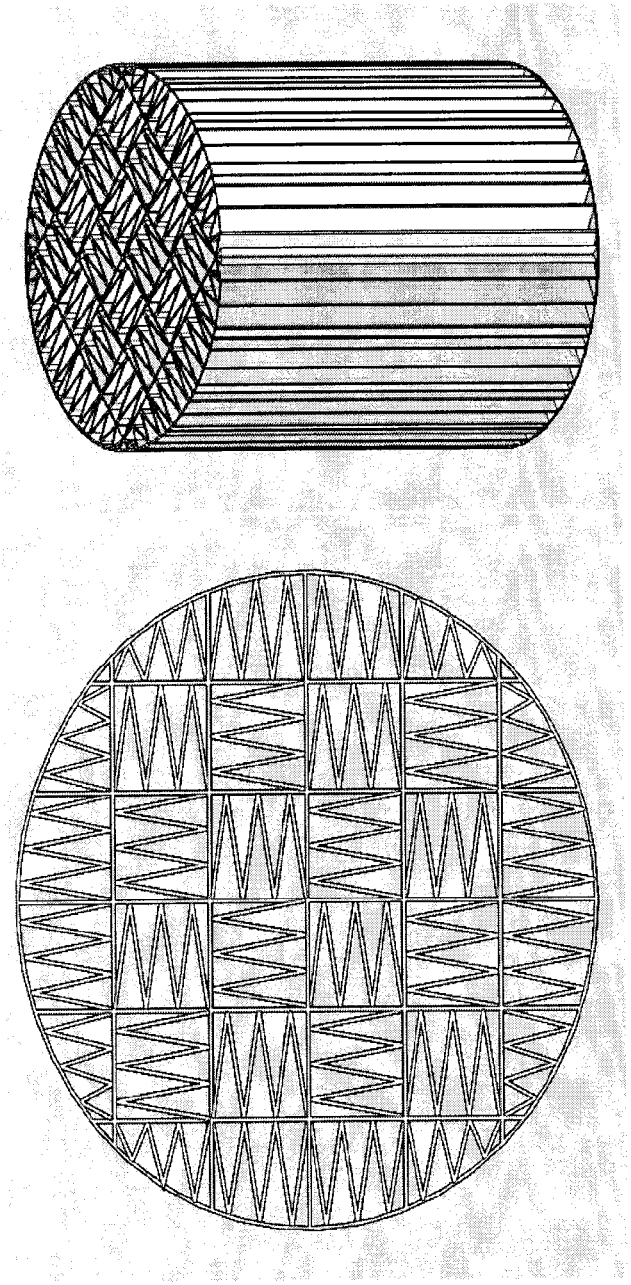
a) Top view  b) Side view
PMD III
FIG. 3.1

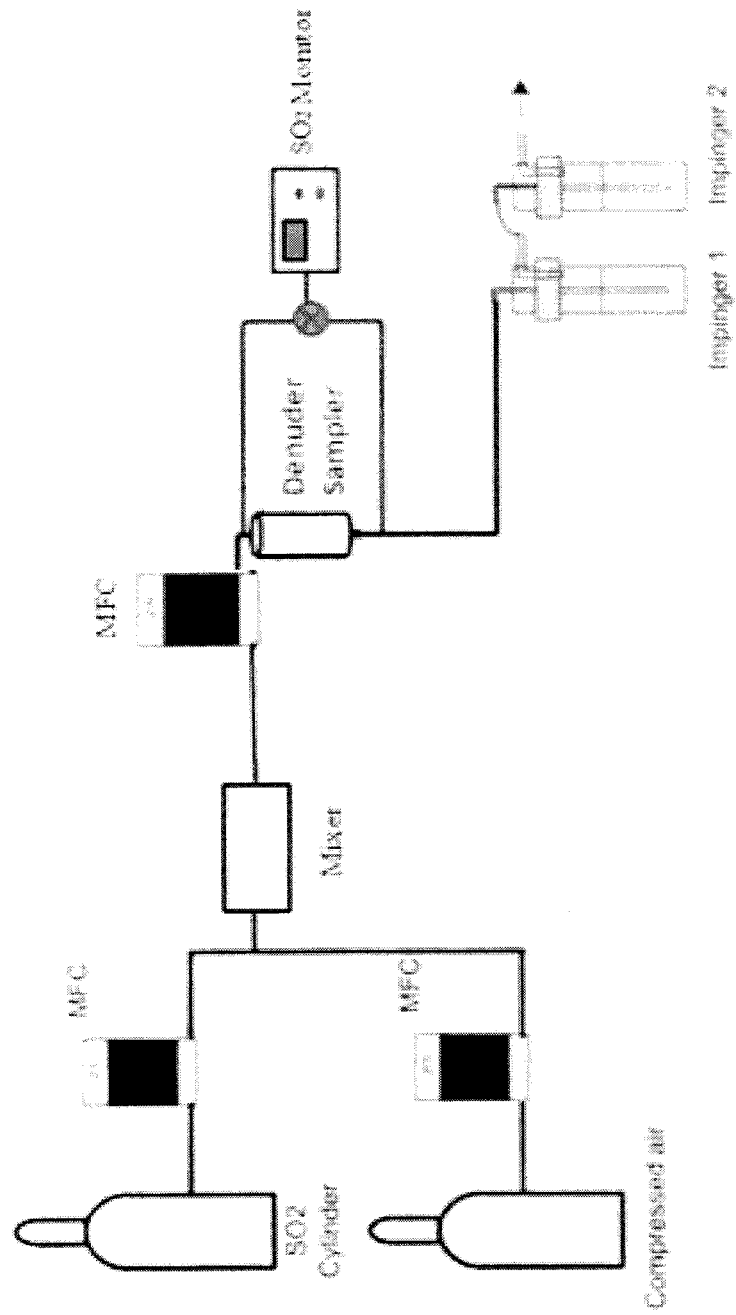
FIG. 3.2

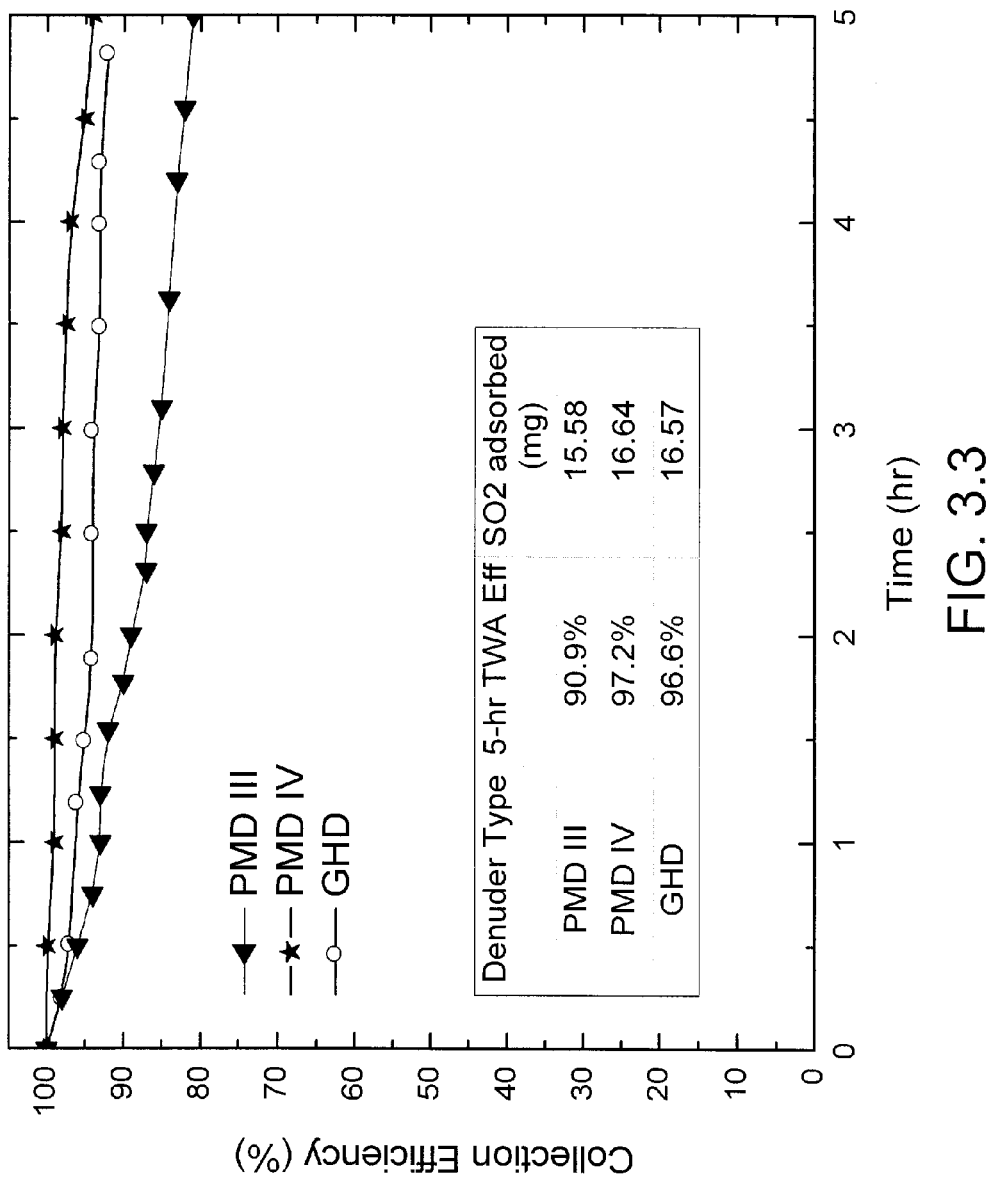
FIG. 3.3

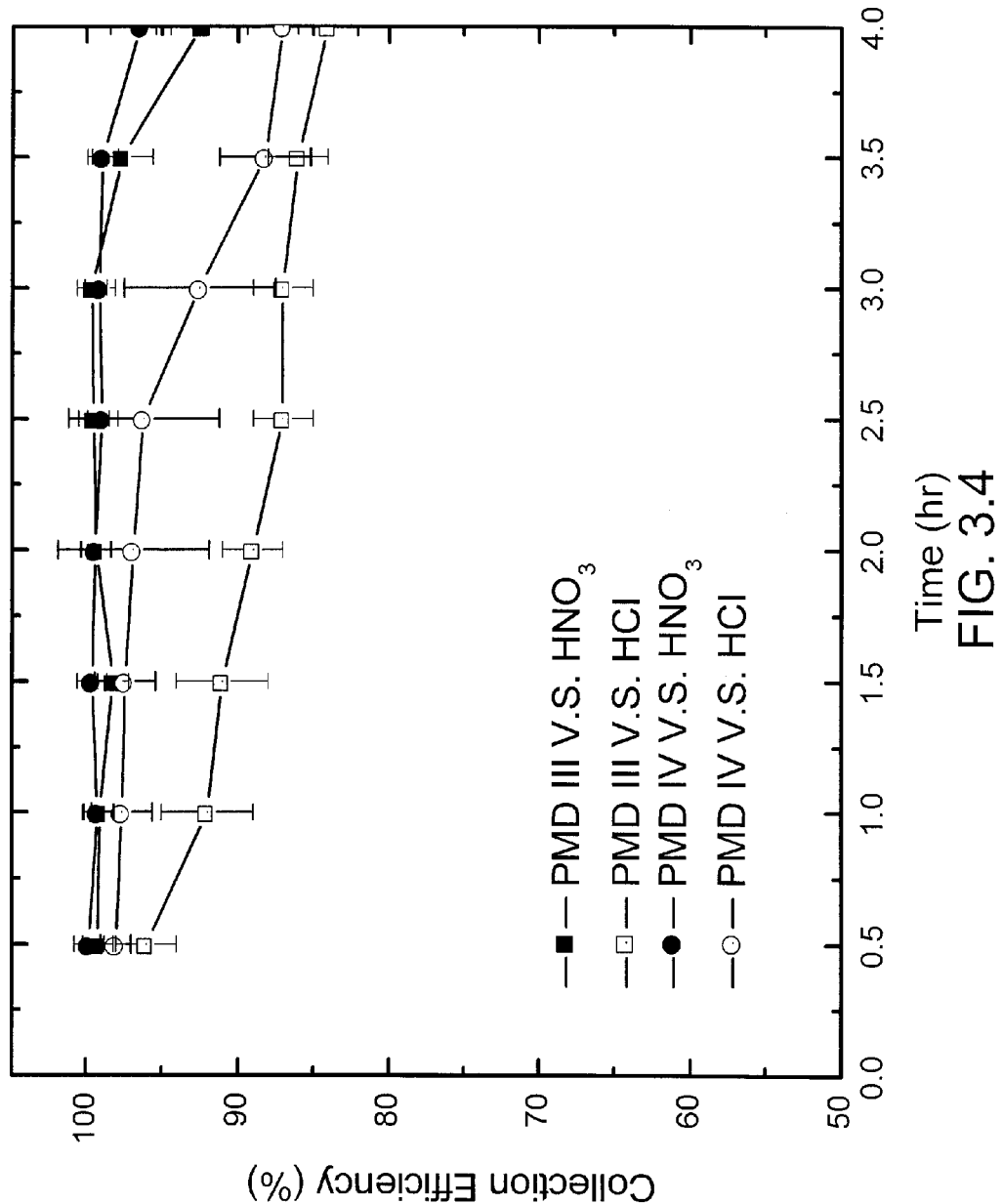
FIG. 3.4

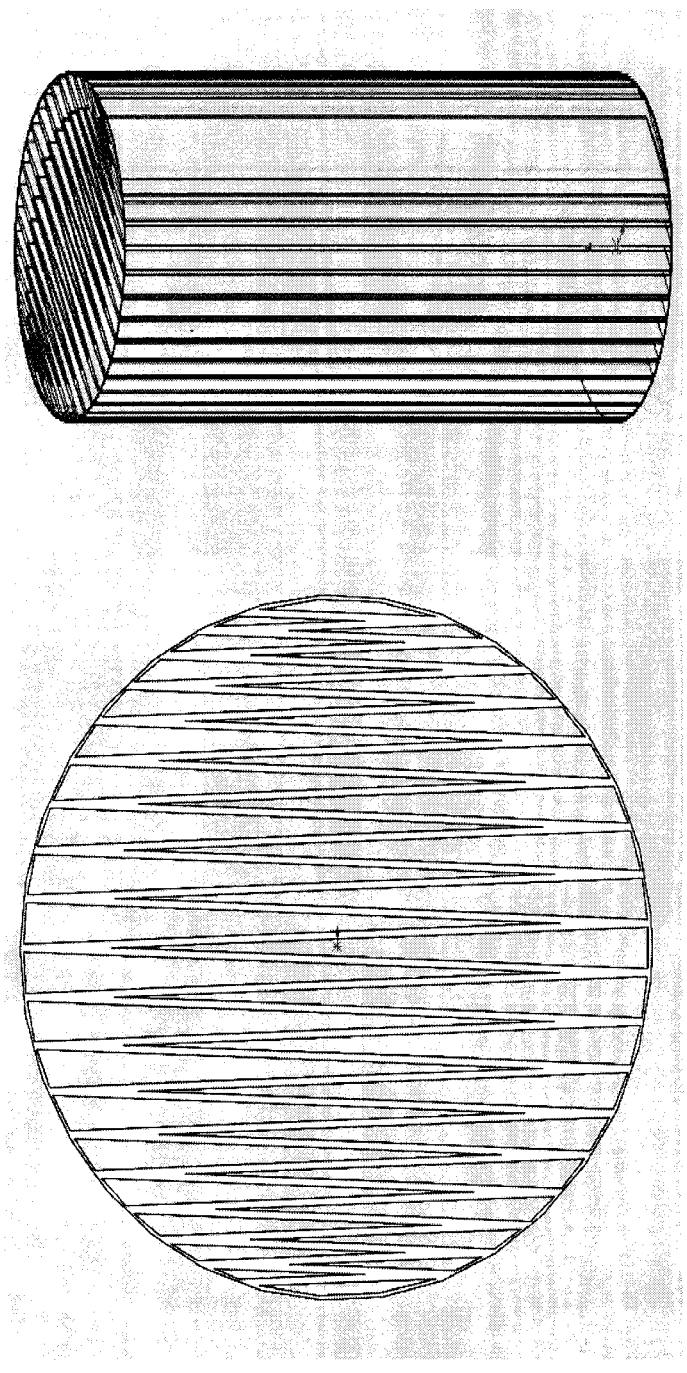
a) Top view   b) Side view
PMD V
FIG. 3.5

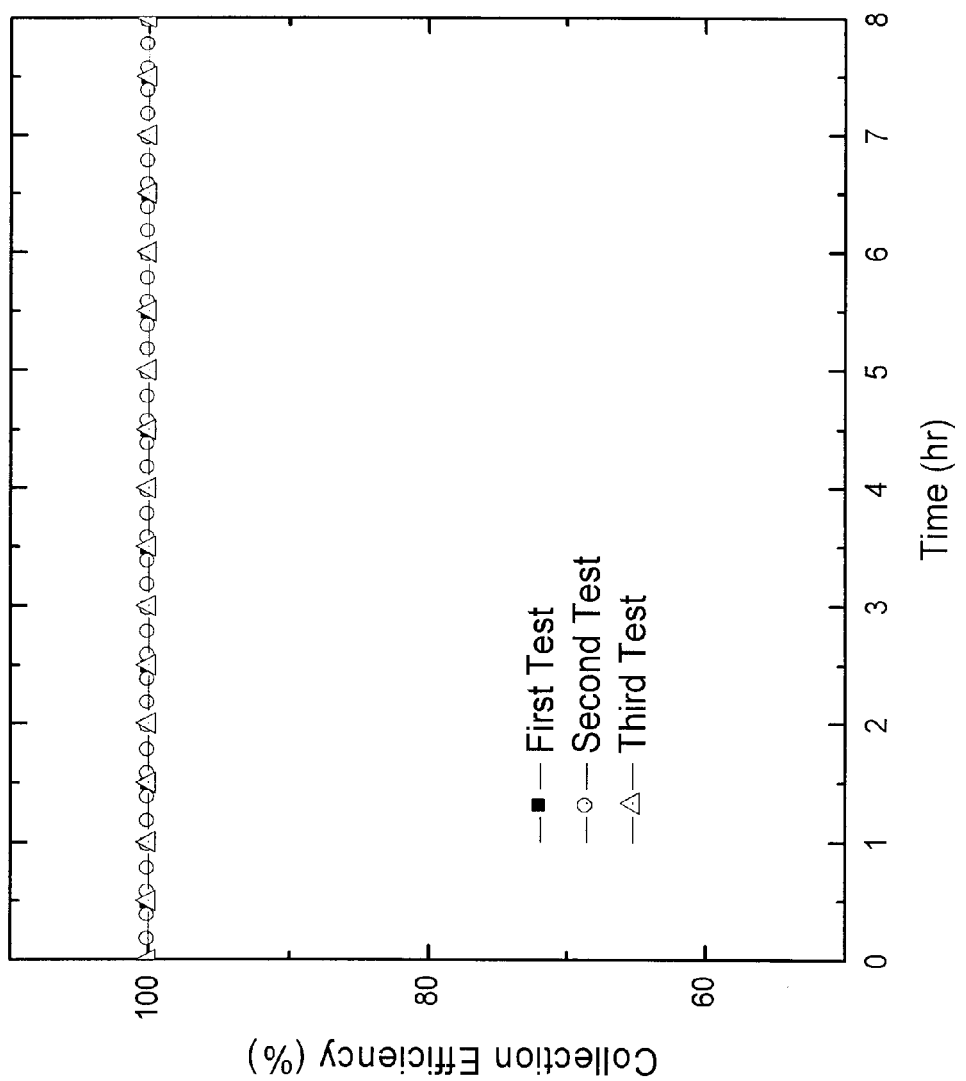
FIG. 3.6

COLLECTING DEVICE FOR GASES AND AEROSOL, METHODS OF MAKING, AND METHODS OF USE

CROSS-REFERENCE TO RELATED APPLICATION(S)

This application is the 35 U.S.C. §371 national stage of PCT application PCT/US2011/56535, filed Oct. 17, 2011 which claims priority to and the benefit of U.S. Provisional Application Ser. No. 61/393,978, filed Oct. 18, 2010, both of which are hereby incorporated by reference herein in their entirety.

STATEMENT OF GOVERNMENT SPONSORSHIP

This invention was made with Government support under Contract/Grant No. FIPR 08-05-069, awarded by the Florida Institute of Phosphate Research. The Government has certain rights in this invention.

BACKGROUND

Various sampling devices have been applied to collect particles or gases, separately. Some researchers have also made effort to sample aerosols and gas simultaneously. To sample acidic gases and aerosols in workplace air, NIOSH Method 7903, which uses one section of glass fiber plug for capturing aerosol followed by two sections of silica gel for collecting gases, is approved by OSHA (Occupational Safety and Health Administration) and commonly used in occupational environments such as phosphate fertilizer manufacturing facilities, sulfuric acid production factories and other industries. However, recent studies have shown sampling artifacts when certain gases are present, e.g., $SO_2$ gas is adsorbed and the extraction process causes artifact sulfuric acid. Therefore, it is necessary to develop a new personal sampler to overcome these deficiencies.

SUMMARY

Embodiments of the present disclosure provide for collection devices, methods of making collection devices, methods of collecting gases and aerosol particles, and the like.

An embodiment of the collection device, among others, includes: a membrane denuder, wherein the membrane denuder is a porous structure that includes at least one chemical composition that collects at least one type of gas; and a filter pack, wherein the filter pack collects aerosol particles that pass through the membrane denuder, wherein the membrane denuder is disposed on top of the filter pack so that the air flow of the gas into the device passes through the membrane denuder before contacting the filter pack. In an embodiment, the collection device also includes an impactor disposed on the membrane denuder on the side opposite the filter pack so that the gas passes through the impactor before contacting the membrane denuder, and wherein the impactor removes large aerosol particles.

An embodiment of the collection device, among others, includes: removing large particles from a gas flow using an impactor; collecting one or more gas types using a membrane denuder after removing the large particles; and collecting one or more aerosol types using a filer pack after collecting the gas using the denuder.

Other structures, methods, features, and advantages of the present disclosure will be, or become, apparent to one with skill in the art upon examination of the following drawings and detailed description. It is intended that all such additional structures, methods, features, and advantages be included within this description, be within the scope of the present disclosure, and be protected by the accompanying claims.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIG. 1.1 illustrates a collection device including a membrane denuder disposed on a filter pack, where the gas enters the membrane denuder from the top and then proceeds to the filter pack.

FIG. 1.2 illustrates another embodiment of the collection device that includes an impactor disposed on the membrane denuder, where the membrane denuder is disposed on the filter pack.

FIG. 1.3 illustrates a more detailed schematic of an embodiment of a collection device.

FIG. 2.1 illustrates the structure of the personal sampler.

FIG. 2.2 illustrates the structure of the impactor.

FIG. 2.3 illustrates exemplary designs of the porous membrane denuder.

FIG. 2.4 shows the cross structure of the denuder.

FIG. 2.5 shows the structure of the filter pack.

FIG. 2.6 illustrates a graph illustrating $SO_2$ removal efficiency of the fabric denuder as a function of time.

FIG. 2.7 illustrates a graph showing the impactor performance compared with respirable convention.

FIG. 2.8 illustrates the particle loss in the denuder.

FIG. 3.1 illustrates schematics of the PMD III.

FIG. 3.2 illustrates the experimental setup for testing gas collection efficiency.

FIG. 3.3 illustrates the $SO_2$ removal efficiency of GHD and PMDs as a function of time.

FIG. 3.4 illustrates PMD III's and IV's capacities for 4 ppm $HNO_3$ and 10 ppm HCl gas.

FIG. 3.5 illustrates schematics of the PMD

FIG. 3.6 illustrates $SO_2$ removal efficiency of PMD V as a function of time.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of environmental engineering, biology, chemistry, materials science, mechanical engineering, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by volume, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequences where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Discussion

In accordance with the purpose(s) of the present disclosure, as embodied and broadly described herein, embodiments of the present disclosure, in one aspect, relate to collection devices, methods of making collection devices, methods of collecting gases and aerosol particles, and the like. An embodiment of the present disclosure can be used as a personal sampler that can sample aerosol and gas simultaneously without interference to each other and can be used in occupational environment where pollutant concentration of the interest is high.

Embodiments of the present disclosure allow for the collection of gases and aerosol particles while preventing either from interfering with the detection of the other (e.g., artifacts that lead to improper determination of the gas(es) and/or aerosol particles present), which is a problem with many other devices and methods. In general, the gas is first collected and then the aerosol particles of interest are collected, and this prevents gases interfering with the aerosol particles collected on the filter surface. Embodiments of the present disclosure can be used to detect gases such as HCl gas, $SO_2$ gas, HF gas, $HNO_3$ gas, and $NH_3$ gas and aerosols such as $H_2SO_4$ and $H_3PO_4$, with less than 5% or without any artifacts.

Industrial hygienists, environmental health and safety personnel and the like, can use embodiments of the present disclosure to characterize hazardous gases and/or aerosols in the work place or at home. Embodiments of the device are modular, small, lightweight and compact (e.g., about 37 mm in diameter and about 50 mm in length) with high capacity (e.g., 100 mg of $SO_2$) so that the device can be worn on a belt or other similar strap so that use of the device is convenient and represents where a person actually works as opposed to a stationary position. Embodiments of the present disclosure can be used in industries such as fertilizer manufacturing, acid production, electroplating, semiconductor, battery, metal smelting, machining, and the like. Meanwhile, the portability of such a compact system also allows it to be deployed for ambient sampling network to cover a wide area or indoor air sampling.

FIGS. 1.1 and 1.2 illustrate two embodiments of the present disclosure. FIG. 1.1 illustrates a collection device including a membrane denuder disposed on a filter pack, where the gas enters the membrane denuder from the top and then proceeds to the filter pack. FIG. 1.2 illustrates another embodiment of the collection device that includes an impactor disposed on the membrane denuder, where the membrane denuder is disposed on the filter pack. FIG. 1.3 illustrates a more detailed schematic of an embodiment of a collection device.

In the embodiments shown in FIGS. 1.2 and 1.3, the air moves through the impactor, through the membrane denuder, and to the filter pack. In either embodiment, the device can include a structure that holds the two or three components and is modular so the membrane denuder and filter pack can be easily removed and analyzed (and replaced). The gas or air flow through the collection device can be controlled by a pump to pull the gas through the collecting device, where the pump pulls from the area below the filter pack.

In an embodiment, the sampling flowrate of the collection device is about 0.5 to 5 Liter per minute. In an embodiment, the collection efficiency of gases of interest is about 80% to 100%. In an embodiment, the collection efficiency of the aerosol particles by the impactor is about 10% to 100%, depending on the particle size, and by the filter pack is about 90% to 100%.

The impactor, when included in the collecting device, can be used to remove large aerosol particles and/or can be used to classify different sizes of aerosol particles. By designing different nozzle numbers and sizes in the impactor, the impactor can follow different particle collection patterns, e.g., human respiratory pattern (respirable fraction, thoracic fraction or inhalable fraction) or air quality standard (PM2.5, PM10).

In an embodiment, the impactor includes one or more inlets to the collection device and one or more exits at the bottom of the impactor on the side adjacent the membrane denuder. In an embodiment, the entrance and the exit are not in line with one another so that large aerosol particles do not flow directly into the membrane denuder. On the bottom portion of the impactor directly below the entrance of the impactor is an aerosol particle impaction plate that can be used to collect large aerosol particles such as inorganic acid particles, metal particles, and dust particles. The aerosol particle impaction plate can be made of materials such as stainless steel alloy or polymer. The selection of materials depends on the specific application of the personal sampler. The ratio of the area of the entrance to the area of the aerosol particle impaction plate can be about 1/10 to 1/1000.

In an embodiment, the size classification can follow human respiratory patterns (respirable fraction or thoracic fraction) to satisfy OSHA regulations or air quality standards satisfying EPA regulations. In an embodiment the impactor can include 2 or more sub-impactors used to classify different aerosol particle sizes (e.g., each sub-impactor has different entrance diameters and exit (to the membrane denuder) diameters). In particular, Example 1 describes an impactor with four sub-impactors to comply with OSHA testing. Additional details are described in Example 1. The diameter (or width) of the impactor can be about 10 mm to 100 mm. The length of the impactor can be about 5 mm to 50 mm.

The membrane denuder operates under the principle of gas diffusion to collect the gas(es) of interest. When air passes through the membrane denuder (i.e., the air flow travels parallel to the membranes), gas molecules diffuse to the membrane denuder walls perpendicular to the flow and are absorbed (collected). The remaining aerosol particles continue to the filter pack positioned below the membrane denuder. In this way, the interference of the gas(es) with the aerosol particles on the filter pact is substantially reduced (e.g., about 75% or more, about 80% or more, about 85% or more, about 90% or more, about 95% or more, or about 99% or more) or eliminated.

In an embodiment, the membrane denuder does not require regeneration.

In an embodiment, the membrane denuder can be a porous structure and can be coated with at least one chemical composition that collects at least one type of gas (e.g., HCl, $SO_2$, HF, $HNO_3$, $NH_3$, Volatile Organic Compounds (VOCs) (e.g., aliphatic hydrocarbons, aromatic hydrocarbons, chlorinated solvents, terpenes, and the like), and combination thereof. In an embodiment the (VOCs can include: toluene, benzene, ethylbenzene, acetone, methyl tert-butyl ether, formaldehyde, ethylene glycol, methylene chloride, dichloromethane, trichloroethane, perchloroethylene, n-butyl acetate, 4-phenylchclohexene, limonene, a-pinene, octane, decane, undecane hexane, isodecane, xylene, and combinations thereof). Chemical compositions of the coating materials and the corresponding gas(es) that can be absorbed are listed in Table 1. The amount of chemical composition can be adjusted depending upon the amount of exposure expected (if known), the different types of gases to be collected, the time of exposure, and the like. The membrane denuder can be made out of materials such as fabric (e.g., cellulose filter, glassfiber filter, membrane filter, Teflon membranes, PTFE), paper, film, and the like.

TABLE 1

Coating materials for absorbing gases in the membrane denuder

| Coating Material | Gas Absorbed | Reference (corresponding to Ex. 1) |
|---|---|---|
| Oxalic acid | $NH_3$, aniline | De Santis and Perrino (1986); Ferm (1979); Cheng (2001) |
| Oleic acid | $SO_3$ | Thomas (1955) |
| $H_3PO_4$ | $NH_3$ | Stevens et al. (1978) |
| $K_2CO_3$ | $SO_2$, $H_2S$ | Durham et al. (1978) |
| $Na_2CO_3$ | $SO_2$, HCl, $HNO_3$, $HNO_2$ | Forrest et al. (1982) |
| $CuSO_4$ | $NH_3$ | Thomas (1955) |
| Citric Acid | $NH_3$ | Langford (1989) |
| $PbO_2$ | $SO_2$, $H_2S$ | Durham et al. (1978) |
| $WO_3$ | $NH_3$, $HNO_3$ | Branman et al. (1982) |
| MgO | $HNO_3$ | Stevens et al. (1978) |
| NaF | $HNO_3$ | Slanina et al. (1981) |
| NaCl | $HNO_3$ | Perrino et al. (1990) |
| NaOH and guaiacol | $NO_2$ | Buttini et al. (1987) |
| Bisulfite-Triethanolamine | Formaldehyde | Cecchini et al. (1985) |
| Gold | Gaseous mercury | Munthe et al. (1990) |
| Activated carbon | Volatile organic compounds | Cooper and Alley (2010) |

In an embodiment, the use of a porous membrane provides a much higher surface area than the solid surface provided by conventional denuders, hence yielding a much larger capacity. The membrane denuder includes walls that are parallel to the gas flow, so that the aerosol particles are not caught in the membrane denuder. The membrane denuder can have a cross-section that is selected from an annular pattern, a swirl pattern, grid pattern, plate pattern, a honeycomb pattern, repetitive "V" pattern, a polygonal pattern, an accordion pattern, or a combination thereof, where the walls are parallel to the gas flow and perpendicular to the filter pack.

In an embodiment, the membrane denuder can have a surface area of about 0.01 $m^2$ to 100 $m^2$ or about 1 $m^2$ to 10 $m^2$. The diameter of the cross-section can be about 10 mm to 100 mm or about 30 mm to 50 mm. The length of the membrane denuder can be about 5 mm to 200 mm or about 10 mm to 100 mm. The ratio of the cross-section of the area occupied by the membrane denuder to the cross-section of the area of unoccupied (e.g., openings in the membrane denuder for particles to fall to the filter pack) is about 0.001 to 0.5.

In an embodiment, the membrane denuder can have a collection capacity of about 0.1 g to 2 g for any one or a combination of the gases listed in Table 1. Collection capacity of the denuder depends on the porosity, length and diameter of the denuder, the coating thickness and concentration of the coating material to the denuder and the diffusion coefficient of the target gas, and the flowrate through the denuder.

In an embodiment, gas(es) of interest can include volatile organic compounds (VOCs), chemical warfare agents, and also include the following: aldehydes, aliphatic nitrogen compounds, sulfur compounds, aliphatic oxygenated compounds, halogenated compounds, organophosphate compounds, phosphonothionate compounds, phosphorothionate compounds, arsenic compounds, chloroethyl compounds, phosgene, cyanic compounds, or combinations thereof. In one embodiment, the contaminant is acetaldehyde, methyl mercaptan, ammonia, hydrogen sulfide, diethyl sulfide, diethyl disulfide, dimethyl sulfide, dimethyl disulfide, trimethylamine, styrene, propionic acid, n-butyric acid, n-valeric acid, iso-valeric acid, pyridine, formaldehyde, 2-chloroethyl ethyl sulfide, carbon monoxide, or combinations thereof.

Embodiments of the present disclosure may include a space between the impactor bottom surface and the membrane denuder and/or a space between the membrane denuder and the filter pack. The space between each can vary depending upon variables such as dimensions of the various components, the pumping speed, and the like.

In an embodiment, the filter pack can include one or more filters (e.g., a first filter and a back up filter (See FIG. 1.3)) disposed on top of one another. In an embodiment, the filter can include filters for collecting aerosols of interest such as $H_2SO_4$ and $H_3PO_4$ particles. In an embodiment, the aerosol particles that are collected on the filter(s) can have a diameter of about 0.01 µm to 100 µm or about 0.01 µm to 10 µm. The filter can be made of a material such as glass fiber, Teflon®, polymer, carbon, ceramic, and a combination thereof. The filter can be a fibrous filter, a porous membrane filter, a granular bed filter, or a combination thereof. A fibrous filter includes fibers having a diameter on the order of about 10 nm to 10 µm. In an embodiment, the diameter of the fibers is about 20 to 80 nm. A porous membrane filter can be a membrane with pores of about 100 nm to 10 µm. A granular bed filter includes granules with pores on each granule and between granules of about 10 nm to 100 µm. The filter can be about 1 µm to 10 cm thick, and the length and width can be on the order of cm to meters depending on the particular application. The type (e.g., material, size, and the like) of filter can depend, at least in part, upon the intended use of the pollutant collection system, the exposure to contaminants, the type of contaminants, and the like.

In an embodiment, the diameter (or the length or width) of the filter(s) can be about 10 mm to 100 mm or about 30 mm to 50 mm. In an embodiment, the thickness of the filter(s) can be about 0.01 mm to 10 mm or about 0.05 mm to 1 mm. Once the air passes through the filter, the air can be directed out of the collection device.

EXAMPLES

Now having described the embodiments of the present disclosure, in general, the examples describe some additional embodiments of the present disclosure. While embodiments of the present disclosure are described in connection with the examples and the corresponding text and figures, there is no intent to limit embodiments of the present disclosure to these descriptions. On the contrary, the intent is to cover all alternatives, modifications, and equivalents included within the spirit and scope of embodiments of the present disclosure.

Example 1

In sampling aerosols, the characteristics of particles of different sizes need to be considered. The hazard caused by inhaled particles depends on their chemical composition and on the site at which they deposit within the respiratory system. Particles which penetrate into the pulmonary regions of lungs are dominantly deleterious for the human body. Impactors are relatively small and can be used to classify particles by particle size. In 1977, Marple et al. proposed a parallel impactor which arranged several impactors with different nozzle sizes in parallel to overcome the sharp penetration characteristics of the impactor. Arranged on a single-stage impactor, the sampling characteristics of the impactor can approximate ACGIH/CEN/ISO-defined respirable or thoracic sampling convention accurately (Marple, 1977; Trakumas and Salter, 2009).

To remove gases from an aerosol stream and measure their concentrations separately, a diffusion denuder system has been widely employed (Acker et al. 2005; Cheng 2001; Dasch et al. 1989; Hayami 2005; Huang et al, 2004; Pathak and Chan 2005; Tsai et al 2004). The original design of the denuder system was a straight tube (Ferm, 1979; Durham et al, 1986) with inner wall coated with various adsorbents to absorb different gaseous species. When air passes through the denuder, gas molecules diffuse to the wall of the tube and get adsorbed on the wall. A variety of denuders have been developed during recent years, e.g. annular denuder (Possanzini et al. 1983); coiled denuder (Pui et al., 1990); honeycomb denuder (Koutrakis et al, 1993; Sioutas et al., 1996); parallel plate denuder (Eatough et al. 1993) and so on. However, all of these denuders have been designed for sampling in the ambient or indoor environment, where pollutant concentration is very low. In order to be used in an occupational environment, the denuder system needs more compact designs to increase its capacity in adsorbing gas. In 2001, Tsai et al. developed a personal porous-metal denuder which specifically worked for adsorbing acidic gases and ammonia gas in occupational environment. Field test results showed that the porous-metal denuder has a very high collection efficiency; however, particle loss in the porous metal disc was also high because particles are forced to penetrate the porous metal discs. Therefore, a new device which has both big capacity for gas absorption and low particle loss rate needs to be developed.

To overcome the limitations discussed above, a new "porous membrane denuder" has been designed. It has both the characteristics of high gas collection efficiency and low particle loss rate. By combining with a parallel impactor and a filter pack to construct a personal sampler to collect aerosol and hazardous gas simultaneously and respectively, this new personal sampler can be used to assess human exposures to a variety of gaseous and particulate air pollutants in both occupational environment and ambient environment. Below is a description of the design of this sampler and its performance evaluation tests to collect sulfur dioxide ($SO_2$) gas and aerosols.

Description of the Sampler:

As shown in FIG. 2.1, the entire sampling system can include 3 main components in series: a parallel impactor at the front (optional), a porous membrane denuder in the middle and a filter pack at the end.

The parallel impactor at the front is used to classify aerosol sizes and remove larger aerosols to prevent their deposition in the following denuder. The design of the parallel impactor is similar to that of Trakumas et al. (2009). It includes 4 parallel and separated impactors. The different nozzle sizes of each impactor have different cut sizes, that when combined, will create a collection efficiency curve that follows a desired pattern, e.g., human respiratory pattern (respirable fraction or thoracic fraction) to satisfy OSHA regulations or air quality stands (PM 2.5, PM 10) satisfying EPA (Environmental Protection Agency) regulations (Marple, 1978; Trakumas et al., 2009).

In this design, the size of each impactor has been calculated to follow the American Conference of Governmental Industrial Hygienists (ACGIH) respirable curve with a cut point of 4 µm. The flowrate through each impactor is controlled using exit orifices. Because the pressure drop across the impactor, $\Delta P$, is equal to the dynamic pressure in the nozzles and the pressure drop across each individual impactor is equal, the exit orifices can be sized using the following equation:

$$Q_1^2\left(\frac{1}{S_{1,in}^2} + \frac{1}{S_{1,out}^2}\right) = Q_2^2\left(\frac{1}{S_{2,in}^2} + \frac{1}{S_{2,out}^2}\right) = \ldots = Q_N^2\left(\frac{1}{S_{N,in}^2} + \frac{1}{S_{N,out}^2}\right) \quad [2]$$

where Q is the flowrate through the individual impactor and and $S_{N,in}$ and $S_{N,out}$ are the areas of the inlet nozzles and outlet orifices, respectively.

FIG. 2.2 shows the structure of the impactor, which includes an inlet nozzle plate and an impactor plate with exit orifices. Above the exit impactor there is a collection substrate of the same shape which is made of cellulose filter to collect particles bigger than the cutsize. After sampling, the filter substrate is removed from the sampler and is analyzed. A gasket between the inlet nozzle plate and the filter impaction substrate divides the impactor into four compartments. Each compartment contains one inlet nozzle, corresponding filter substrate and exit orifice. Parameters of these nozzles are presented in Table 1 using a flowrate of 2 L/min.

TABLE 1

Specifications of Impactor nozzle sizes

| $D_{50}$ (μm) | $D_{in}$ (cm) | $D_{out}$ (cm) |
|---|---|---|
| 6.6 | 0.236 | 0.115 |
| 4.6 | 0.186 | 0.125 |
| 3.5 | 0.156 | 0.139 |
| 2.2 | 0.115 | 0.236 |

The porous membrane denuder in the middle is composed of a soft and porous membrane (e.g., fabric, paper, film) coated with a specific chemical to selectively collect target gases by diffusion. The high surface area resulting from the porosity enables high collection capacity in small volume that is important for high concentration scenarios commonly encountered in industrial settings. The flexibility of the membrane also allows diverse configurations of the design (e.g., grid, swirl, as shown in FIG. 2.3) that can maximize available surface area and reduce diffusion distance while maintaining low aerodynamic drag. The denuder wall is parallel to the air flow at all times. Gas is absorbed on the denuder wall by diffusion. Hence, there is no inherent impaction of particles on the denuder.

FIG. 2.4 shows the cross structure of the denuder. The denuder is 50 mm in height and 37 mm in diameter and is constructed of cellulose filter paper, which was selected because of its rigidity and ease in making the cross shape. In addition, cellulose filter is used in NIOSH Method 6004 to absorb sulfur dioxide which provides sufficient background information for our experiment.

The filter pack of selected filters is to collect the penetrating fine aerosols. There are two filters in the filter pack. The first filter collects aerosols that pass through the denuder. The second filter, coated with $Na_2CO_3$, collects acidic gases that evolve from collected aerosols on the first filter. A filter holder with a diameter of 37 mm is used to support the filters. FIG. 2.5 shows the structure of the filter pack.

The 3 components, impactor, denuder, and filter pack, are packaged as modules; thus, it is easy to install and to dissemble. When mixed air flow passes through this personal sampler, larger aerosols will be removed from the gas stream by the impactor, then target gases will be removed by the denuder and finally the remaining fine aerosols will be collected on the filter pack.

$SO_2$ Collection Efficiency and Capacity of the Porous Membrane Denuder

Experiments for measuring gas collection efficiency of the porous membrane denuder were conducted using $SO_2$, supplied from a $SO_2$ cylinder of known concentration at a flowrate of 2 L/min. The porous membrane denuder, two in series, was coated with 15% (w/v) $Na_2CO_3$/1% glycerin and dried. 9 mM $Na_2CO_3$ solution was used in the impingers downstream to absorb gas that penetrated the denuder. Solution in the impinger was then analyzed by an ion chromatography (IC) system. By calculating the penetrating amount of the gas, the collection efficiency of the denuder for $SO_2$ gas could be determined accordingly.

FIG. 2.6 shows the collection efficiency of the denuder under different $SO_2$ feed concentrations. In the first situation, the concentration of $SO_2$ gas was 10 ppm, which is twice the Permissible Exposure Level (PEL) of $SO_2$ set by OSHA. Two denuders were arranged in series to ensure high collection efficiency in a relatively long time period. The experimental result showed that $SO_2$ removal efficiency of the fabric denuder maintained above 95% for about four hours. In the second situation, $SO_2$ gas of 1 ppm passed through one denuder. The collection efficiency of the denuder remained 100% for 8 hours. Prior research showed that SO2 concentration at the phosphate fertilizer plants ranged from 34 ppb to 5.6 ppm, while at most sites the concentration was much lower than 1 ppm (Hsu, 2008). Combined with the experimental result stated above, we can see that two denuders in series in the personal sampler can ensure high $SO_2$ collection efficiency in eight-hour sampling in most conditions. If workers should stay in place where high $SO_2$ concentration is possible for a long time, e.g., attack tank area and sulfuric acid pump tank area, the personal sampler can maintain an efficiency higher than 95% for four hours. However, concerning worker health, it is not appropriate for workers to stay at places with high $SO_2$ concentration for more than two hours.

Aerosol Collection Efficiency and Loss

For measuring particle collection efficiency of the impactor, a vibrating orifice aerosol generator (VOAG, Model 3450, TSI Inc.) was used to generate monodisperse particles of uranine tagged oleic acid. Sampling flowrate of the personal sampler was controlled at 2 L/min to be consistent with that used for the denuder.

An UV-Aerodynamic Particle Sizer (APS, TSI, Model 3012A) was connected to the upstream and downstream of the impactor to measure particle's aerodynamic diameter and number/mass concentration at the two sides. At both upstream and downstream sampling points, the sampling time was 1 minute and it was repeated for 20 times. The geometric standard deviation for feed aerosol diameter was less than 1.2. And then, the means of geometric mean diameter and number concentration for each group of samples were calculated. Finally, penetration percentages of each particle size were obtained by dividing the mean number concentration downstream the impactor over that upstream the impactor.

$$\text{Penetration \%} = \frac{\text{Mass on after filter}}{\text{Mass on after filter} + \text{Mass on filter impaction substrate}} \times 100\%$$

FIG. 2.7 shows the penetration characteristics of the impactor. The solid and dashed curves represent the respirable convention and the theoretical characteristic of the impactor, respectively. Triangle and square points in FIG. 2.7 are two groups of experimental data. We can see from FIG.

2.7 that the overall tendency of the experimental data was in excellent accordance with the respirable curve.

To test particle loss in the denuder, the VOAG was also used to produce monodisperse particles of various sizes. The sampling tubes of the UV-APS were located at upstream and downstream of the denuder. Sampling period was 1 minute with 20 replications, as in aerosol collection test. The mean number concentration before and after the denuder were close to one other, as shown in FIG. 2.8. Number concentration for different particle sizes was slightly different due to different dilution air flow rates and frequencies used in the test. Particle loss was under 5% for particle size from 1 to 10 μm. Particle loss percent of each aerodynamic diameter is also shown in FIG. 2.8.

Conclusion

A novel personal sampler, which includes a parallel impactor, a porous membrane denuder and a filter pack, has been designed, built and tested. The porous membrane denuder was proven to maintain a collection efficiency of $SO_2$ gas higher than 95% for four hours with a feed concentration of 10 ppm and 100% for eight hours with a feed concentration of 1 ppm, which showed that the capacity of the denuder is large enough for measurement in both occupational and ambient environments. The experiments also show that aerosol penetration characteristic of the parallel impactor follows the ACGIH respirable curve excellently and particle loss in the denuder for particles of 1 to 10 μm are under 5%.

References, Each of Which is Incorporated Herein by Reference

Acker, K., Moller, D., Auel, R., Wieprecht, W., and Kalass, D. (2005). "Concentrations of nitrous acid, nitric acid, nitrite and nitrate in the gas and aerosol phase at a site in the emission zone during ESCOMPTE 2001 experiment." *Atmospheric Research*, 74(1-4), 507-524.

Bartley D L, Chen C C, Song R and Fischbach T J (1994) Respirable Aerosol Sampler Performance Testing Am. Ind. Hyg. Assoc. J. 55 1036-1046

Braman, R. S., Shelley, T. J., and Mcclenny, W. A. (1982). "Tungstic Acid for Pre-Concentration and Determination of Gaseous and Particulate Ammonia and Nitric-Acid in Ambient Air." *Analytical Chemistry*, 54(3), 358-364.

Buttini, P., Dipalo, V., and Possanzini, M. (1987). "Coupling of Denuder and Ion Chromatographic Techniques for NO2 Trace Level Determination in Air." *Science of the Total Environment*, 61, 59-72.

Buttini, P., Dipalo, V., and Possanzini, M. (1987). "Coupling of Denuder and Ion Chromatographic Techniques for NO2 Trace Level Determination in Air." *Science of the Total Environment*, 61, 59-72.

Chen C C and Huang S H (1999) Shift of Aerosol Penetration in Respirable Cyclone Samplers Am. Ind. Hyg. Assoc. J. 60 720-729

Cheng, Y. S. (2001). "Condensation Detection and Diffusion Size Separation Techniques." Aerosol Measurement: Principles, Techniques, and Applications, P. A. Baron and K. Willeke, eds., Wiley, N.Y., 569-601.

DeSantis, F., and Perrino, C. (1986). "Personal Sampling of Aniline in Working Sites by Using High-Efficiency Annular Denuders." *Annali Di Chimica*, 76(9-10), 355-364.

Dasch, J. M., Cadle, S. H., Kennedy, K. G., and Mulawa, P. A. (1989). "Comparison of Annular Denuders and Filter Packs for Atmospheric Sampling." *Atmos. Environ.*, 23(12), 2775-2782.

Durham, J. L., Ellestad, T. G., Stockburger, L., Knapp, K. T., and Spiller, L. L. (1986). "A Transition-Flow Reactor Tube for Measuring Trace Gas Concentrations." *Journal of the Air Pollution Control Association*, 36(11), 1228-1232.

Durham, J. L., Wilson, W. E., and Baker Bailey, E. (1978). "Application of an S02-denuder for Continuous Measurement of Sulfur in Submicrometric Aerosols." *Atmos. Environ.*, 12(4), 883-886.

Eatough, D. J., Wadsworth, A., Eatough, D. A., Crawford, J. W., Hensen, L. D., and Lewis, E. A. (1993). "A Multi-System, Multi-Channel Diffusion Denuder Sampler for the Determination of Fine-Particulate Organic Material in the Atmosphere." *Atmos. Environ.*, 27(8), 1213-1219.

Ferm, M. (1979). "Method for Determination of Atmospheric Ammonia." *Atmos. Environ.*, 13(10), 1385-1393.

Forrest, J., Spandau, D. J., Tanner, R. L., and Newman, L. (1982). "Determination of Atmospheric Nitrate and Nitric-Acid Employing a Diffusion Denuder with a Filter Pack." *Atmospheric Environment*, 16(6), 1473-1485.

Gorner P, Wrobel R, Micka V, Skoda V, Denis J and Fabries J F (2001) Study of Fifteen Respirable Aerosol Samplers Used in Occupational Hygiene Ann. Occup. Hyg. 45 43-54

Hayami, H. (2005). "Behavior of secondary inorganic species in gaseous and aerosol phases measured in Fukue Island, Japan, in dust season." *Atmospheric Environment*, 39(12), 2243-2248.

Hinds, W. C. 1999. Aerosol Technology: properties, behavior, and measurement of airborne particles. 483. John Wiley & Sons, Inc.

Hsu, Y.-M., J. Kollett, K. Wysocki, C.-Y. Wu, D. A. Lundgren & B. K. Birky (2007) Positive Artifact Sulfate Formation from SO2 Adsorption in the Silica Gel Sampler Used in NIOSH Method 7903. *Environmental Science & Technology*, 41, 6205-6209.

Huang, Z., Harrison, R. M., Allen, A. G., James, J. D., Tilling, R. M., and Yin, J. X. (2004). "Field intercomparison of filter pack and impactor sampling for aerosol nitrate, ammonium, and sulphate at coastal and inland sites." *Atmospheric Research*, 71(3), 215-232.

Kenny L C, A. R. B. P. E. J. B. G. C. a. M. A. D. (1999) The Sampling Efficiency of Personal Inhalable Aerosol Sampler in Low Air Movement Environments. 30, 627.

Koutrakis, P., A. M. Fasano, J. L. Slater, J. D. Spengler, J. F. McCarthy & B. P. Leaderer (1989) Design of a personal annular denuder sampler to measure atmospheric aerosols and gases. *Atmospheric Environment* (1967), 23, 2767-2773.

Langford, A., Goldan, P., Fehsenfeld, F., (1989) A Molybdenum Oxide Annular Denuder System for Gas Phase Ambient Ammonia Measurements, *Journal of Atmospheric Chemistry*, 8, 359-376

Liden G and Kenny L C 1993 Optimization of the Performance of Existing Respirable Dust Samplers Appl. Occup. Environ. Hyg. 8 386-391

Marple, V. A. (1978) Simulation of Respirable Penetration Characteristics by Inertial Impaction. 9, 125.

Marple, V. A., Benjamin Y. H. Liu (1974) Characteristics of laminar jet impactors. *Environ. Sci. Technol.*, 8, 648-654.

Munthe, J., W. H. Schroeder, Z. Xiao & O. Lindqvist (1990). "Removal of gaseous mercury from air using a gold coated denuder". *Atmospheric Environment*. Part A. General Topics, 24, 2271-2274.

Pathak, R. K., and Chan, C. K. (2005). "Inter-particle and gas-particle interactions in sampling artifacts of PM2.5 in filter-based samplers." *Atmospheric Environment*, 39(9), 1597-1607.

Pavlish, J. H., E. A. Sondreal, M. D. Mann, E. S. Olson, K. C. Galbreath, D. L. Laudal & S. A. Benson (2003) Status review of mercury control options for coal-fired power plants. *Fuel Processing Technology*, 82, 89-165.

Perrino, C., De Santis, F. and Febo, A. (1990). "Criteria for the choice of a denuder sampling technique devoted to the measurement of atmospheric nitrous and nitric acids", *Atmospheric Environment* 24A, pp. 617-626.

Philip Demokritou, I. G. K., Stephen T. Ferguson, and Petros Koutrakis (2001) Development and Laboratory Performance Evaluation of a Personal Multipollutant Sampler for Simultaneous Measurements of Particulate and Gaseous Pollutants. *Aerosol Science and Technology*, 35, 741-752.

Possanzini, M., Febo, A., and Liberti, A. (1983). "New Design of a High Performance Denuder for the Sampling of Atmospheric Pollutants." *Atmospheric Environment*, 17(12), 2605-2610.

Pui, D. Y. H., Lewis, C. W., Tsai, C. J., and Liu, B. Y. H. (1990). "A Compact Coiled Denuder for Atmospheric Samplingt." *Environ Sci. Technol.*, 24(3), 307-312.

Slanina, J., Lamoendoornenbal, L. V., Lingerak, W. A., Meilof, W., Klockow, D., and Niessner, R. (1981). "Application of a Thermo-Denuder Analyzer to the Determination of H2SO4, HNO3 and NH3 in Air." *International Journal of Environmental Analytical Chemistry*, 9(1), 59-70.

Sioutas, C., Wang, P. Y., Ferguson, S. T., and Koutrakis, P. (1996). "Laboratory and Field Evaluation of an Improved Glass Honeycomb Denuder/Filter Pack Sampler." *Atmos. Environ.*, 30(6), 885-895.

Stevens, R. K., Dzubay, T. G., Russwurm, G., and Rickel, D. (1978). "Sampling and Analysis of Atmospheric Sulfates and Related Species." *Atmospheric Environment*, 12(1-3), 55-68.

Thomas, J. W. (1955). "The Diffusion Battery Method for Aerosol Particle Size Determination." *Journal of Colloid and Interface Science*, 10, 246-255.

Trakumas, S. a. S., E. (2009) Parallel particle impactor—novel size-selective particle sampler for accurate fractioning of inhalable particles. *Journal of Physics*, 151, 012060.

Tsai, C. J., Huang, C. H., and Lu, H. H. (2004). "Adsorption capacity of a nylon filter of filter pack system for HCl and HNO3 gases." *Separation Science and Technology*, 39(3), 629-643.

Tsai, C. J., Huang, C. H., Wang, S. H., and Shih, T. S. (2001b). "Design and Testing of a Personal Porous-Metal Denuder." *Aerosol Sci. Tech.*, 35(1), 611-616.

Wright, B. M. (1954) A size-selecting sampler for airborne dust. *Brit. J. industr. Med.*, 11, 284-288.

Example 2

Experimental System and Procedures

Material

To compare the porous membrane denuder's (PMD) capacities with commercially available denuder, experiments were carried out with PMD III, PMD IV (i.e., $3^{rd}$ and $4^{th}$ generation) and a glass honeycomb denuder (GHD). The GHD has been commercialized and integrated in a denuder-filter system, which is called "ChembComb Speciation Sampling Cartridge" (Model 3500, Thermo Electron Co., Inc.). The GHD is 47 mm in diameter and 38 mm long. Its internal surface area of 508 $cm^2$ is made possible by 212 hexagonal flow channels that are 2 mm on each side. The GHD has a weight of 106 g. The schematic of PMD III is shown in FIG. 3.1. PMD IV has the same structure as PMD III, only with more zigzag inserts. Properties of the PMDs and GHD are listed in Table 1. Both the PMDs and GHD were coated with 10% sodium carbonate ($Na_2CO_3$)/glycerin to absorb $SO_2$ and other acidic gases.

TABLE 1

Properties of PMD III, PMD IV and GHD

| Denuder | Diameter (mm) | Length (mm) | Number of Channels | Channel opening area ($mm^2$) | Weight (g) |
|---|---|---|---|---|---|
| PMD III | 47 | 50 | 192 | 8.58 | 6~9 |
| PMD IV |  | 50 | 280 | 5.90 |  |
| GHD |  | 38 | 212 | 6.88 | 106 |

Sampling and Analysis

Denuder Collection Efficiency

The experimental system for capacity test is shown in FIG. 3.2. In testing PMDs' performance in occupational environment, the feed $SO_2$ concentration used was 10 ppm, which is twice the Permissible Exposure Level (PEL) of $SO_2$ set by U.S. Occupational Safety and Health Administration (OSHA). The flow rate of the gas stream, 2 L/min, was controlled by a mass flow controller (MFC; OMEGA, Model FMA 5520). An $SO_2$ monitor (International Sensor Technology, Inc., Model IQ-350) which can monitor the $SO_2$ concentration in real time was connected to the upstream and downstream of the sampler to measure $SO_2$ gas concentrations. Two impingers in series were connected downstream of the sampler using 9 mM $Na_2CO_3$ solution to absorb gas that penetrated the denuder. Solution in the two impingers was changed every 30 minutes. Most of the exhaust gas was collected by the first impinger, while the second impinger was used to check whether the first one broke through. After sampling, hydrogen peroxide ($H_2O_2$) was added to the sample solution to oxidize sulfite to form sulfate. Time weighted average (TWA) concentration of sulfate ions was determined by an IC system (Model ICS-1500, DIONEX Inc.).

For real-time gas monitoring using the $SO_2$ monitor, the collection efficiency (Eff) of $SO_2$ can be obtained by measuring the feed concentration ($C_u$) upstream and the exit concentration ($C_d$) downstream of the personal sampler. Eff at any given time can be calculated by the following equation:

$$Eff = \frac{c_u - c_d}{c_u} = 1 - \frac{c_d}{c_u} \qquad (1)$$

When the impinger method was used for measuring downstream gas concentration, the exit gas concentration in Equation (1) was the summation of the concentrations in impingers 1 and 2.

In addition to testing $SO_2$, the system has also been tested for 10 ppm HCl and 4 ppm $HNO_3$ using PMD III and PMD IV. Both concentrations correspond to twice their OSHA standards.

Results and Discussion

The collection efficiencies of the two different types of PMDs and the GHD are shown in FIG. 3.3. It can be seen that as the number of channels increases and channel cross-sectional area decreases, the capacity of the denuder increases. 5-hour TWA collection efficiencies of PMD III, and IV were 90.9% and 97.2%, respectively, while that of the GHD was 96.6%. Compared with the GHD, PMD IV has slightly higher collection efficiency. However, the weight of the GHD is about 10 times greater than that of the PMD IV. In addition, since the PMDs are made of filter paper, they are relatively cheap. Furthermore, they are disposable and therefore users do not have to be concerned if the unit contains residual from the previous test. These advantages make the PMDs superior to traditional denuders made of glass or metals for applications where light weight, low cost and ease of operation are important features.

The results for testing HCl and $HNO_3$ are displayed in FIG. 3.4. As shown, PMD III and IV are more efficient for collecting $HNO_3$ than HCl due to lower $HNO_3$ feed concentration. PMD IV, which has more channels, has excellent performance for both gases in the entire 4 hours.

Testing of PMD V

PMD V was specially designed to have a more flexible structure. Cellulose membrane (Whatman Grade 40) was cut by a laser plotter into an accordian shape cross-section. When folded, the edges of the PMD fitted the cylindrical denuder system very well, as shown in FIG. 3.5. The development of PMD V shows the flexibility of porous membrane in constructing denuders of various shapes. In addition, compared to multi-grid construction of PMD III and IV, PMD V is much easier to fabricate and assemble. It is also easier to adopt PMD V to smaller or longer sampling system.

PMD V developed in this test was 70 mm long and 20 mm in diameter (when folded). It was coated with 10% (w/v) $Na_2CO_3$/glycerin solution and dried before experiments. PMD V's capacity for $SO_2$ gas of 10 ppm was tested. Experimental system is shown in FIG. 3.2. Sampling flow rate was kept at 2 L/min. In all three experiments, PMD V exhibited a collection efficiency of 100% for 8 hours, as shown in FIG. 3.6. It is clear that PMD V has capacity high enough for applications to occupational sampling.

References, Which are Incorporated Herein by Reference

Koutrakis P., Wolfson J. M., Slater J. L., Brauer M., Spengler J. D., Stevens R. K. and Stones C. L. (1988) Evaluation of an annular denuder/filter pack system to collect acidic aerosols and gases. *Enuir. Sci. Technol.* 22, 1463-1468.

Ianniello, A., Beine, H. J., Landis, M. S., Stevens, R. K., Esposito, G., Amoroso, A. and Allegrini, I. (2007). Comparing field performances of denuder techniques in the high Arctic. Atmospheric Environment, 41(8), 1604-1605

Trakumas, S. and Salter, E. (2009) Parallel particle impactor—novel size-selective particle sampler for accurate fractioning of inhalable particles. *Journal of Physics: Conference Series,* 151, 012060.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A collection device, comprising:
a membrane denuder, wherein the membrane denuder is a flexible fabric porous structure that includes at least one chemical composition that collects at least one type of gas; and
a filter pack, wherein the filter pack collects aerosol particles that pass through the membrane denuder, wherein the membrane denuder is disposed on top of the filter pack so that the air flow of the gas into the device passes through the membrane denuder before contacting the filter pack an impactor disposed on the membrane denuder on the side opposite the filter pack so that the gas passes through the impactor before contacting the membrane denuder, and wherein the impactor removes large aerosol particles; and wherein the membrane denuder includes porous walls that are parallel to the air flow and perpendicular to the filter pack.

2. The collection device of claim 1, wherein the impactor includes two or more inlet orifices and exit orifice, wherein dimensions of the inlet orifices are different, and wherein the inlet orifices are used to classify different sizes of aerosol particles.

3. The collection device of claim 1, wherein the chemical composition has an affinity for one or more of the following: HCl gas, $SO_2$ gas, HF gas, $HNO_3$ gas, $NH_3$ gas and volatile organic compounds.

4. The collection device of claim 1, wherein the filter pack filters out aerosols selected from the group consisting of $H_2SO_4$ and $H_3PO_4$.

5. The collection device of claim 1, wherein the chemical composition has an affinity for one or more of the following: HCl gas, $SO_2$ gas, HF gas, $HNO_3$ gas, $NH_3$ gas, and volatile organic compounds, and wherein the filter pack filters out aerosols selected from the group consisting of $H_2SO_4$ and $H_3PO_4$, wherein collection of the gas and aerosols simultaneously does not result in interference between the gas and aerosol.

6. The collection device of claim 1, wherein the membrane denuder has a cross-section that is selected from a swirl pattern, grid pattern, plate pattern, polygonal pattern, multi-annular pattern, a honeycomb pattern, a repetitive "V" pattern, an accordion pattern, and a combination thereof.

7. A method of collecting aerosol particles and collecting gas, comprising:
removing large particles from a gas flow using an impactor;
collecting one or more gas types using a membrane denuder after removing the large particles, wherein the membrane denuder is a flexible fabric porous structure that includes at least one chemical composition that collects at least one type of gas; and
collecting one or more aerosol types using a filer pack after collecting the gas using the membrane denuder wherein the membrane denuder includes porous walls that are parallel to the air flow and perpendicular to the filter pack.

8. The method of claim 7, wherein the chemical composition has an affinity for one or more of the following: HCl gas, $SO_2$ gas, HF gas, $HNO_3$ gas, $NH_3$ gas, and volatile organic compounds.

9. The method of claim 7, wherein the filter pack collects aerosols selected from the group consisting of $H_2SO_4$ and $H_3PO_4$.

10. The method of claim 7, wherein the chemical composition has an affinity for one or more of the following: HCl gas, $SO_2$ gas, HF gas, $HNO_3$ gas, $NH_3$ gas, and volatile organic compounds, and wherein the filter pack collects aerosols selected from the group consisting of $H_2SO_4$ and $H_3PO_4$, wherein collection of the gas and aerosols simultaneously does not result in interference between the gas and aerosol.

11. The method of claim 7, wherein the membrane denuder has a high surface area and open porous structure that allows more efficient absorption and higher capacity of gas molecular than solid surface denuders.

12. The method of claim 7, wherein the membrane denuder does not require regeneration.

13. The method of claim 7, wherein the membrane denuder has a cross-section that is selected from a swirl pattern, grid pattern, plate pattern, polygonal pattern, multi-annular pattern, a honeycomb pattern, a repetitive "V" pattern, an accordion pattern, and a combination thereof.

* * * * *